United States Patent
Hanina et al.

(10) Patent No.: US 10,918,331 B2
(45) Date of Patent: Feb. 16, 2021

(54) METHOD AND APPARATUS FOR DETERMINING HEALTH STATUS

(71) Applicant: AIC Innovations Group, Inc., New York, NY (US)

(72) Inventors: Adam Hanina, New York, NY (US); Daniel Glasner, New York, NY (US); Li Zhang, Princeton, NJ (US)

(73) Assignee: AIC Innovations Group, Inc., New York, NY (US)

( * ) Notice: Subject to any disclaimer, the term of this patent is extended or adjusted under 35 U.S.C. 154(b) by 13 days.

(21) Appl. No.: 16/134,516

(22) Filed: Sep. 18, 2018

(65) Prior Publication Data
US 2019/0083031 A1 Mar. 21, 2019

Related U.S. Application Data

(60) Provisional application No. 62/560,523, filed on Sep. 19, 2017.

(51) Int. Cl.
*A61B 5/00* (2006.01)
*G06T 7/00* (2017.01)
(Continued)

(52) U.S. Cl.
CPC .......... *A61B 5/4842* (2013.01); *A61B 5/0077* (2013.01); *A61B 5/0205* (2013.01);
(Continued)

(58) Field of Classification Search
CPC ......... A61B 5/4082; A61B 5/163; A61B 5/05; A61B 5/1071; A61B 5/112; A61B 5/1124;
(Continued)

(56) References Cited

U.S. PATENT DOCUMENTS 8,666,781 B2  3/2014 Hanina et al.
8,731,961 B2  5/2014 Hanina et al.
(Continued)

FOREIGN PATENT DOCUMENTS

WO   WO 2016/074036   5/2016

OTHER PUBLICATIONS

International Search Report and Written Opinion for Int. App No. PCT/US2018/051480, dated Dec. 6, 2018 (6 pages).
(Continued)

*Primary Examiner* — Erin M Piateski
(74) *Attorney, Agent, or Firm* — Fish & Richardson P.C.

(57) ABSTRACT

Systems and methods for determining a heath status of a patient through an automated interview. One of the systems include one or more computers in one or more locations and one or more storage devices storing instructions that, when executed by one or more computers, cause the one or more computers to perform operations including: providing, to a user interface of a user device, questions for a user to respond to in an interactive manner, in which each of the questions following the first questions is adaptive based on the user's response to one or more of the previous questions; capturing motion and appearance of the user in a video sequence while the user is responding to the questions; and analyzing the motion of the user in the video sequence to determine one or more indications of a disease or of a change in a disease progression.

21 Claims, 5 Drawing Sheets

(51) Int. Cl.
- G06T 7/20 (2017.01)
- A61B 5/0205 (2006.01)
- A61B 5/11 (2006.01)
- G16H 50/30 (2018.01)
- G16H 20/00 (2018.01)
- G16H 30/40 (2018.01)
- G16H 40/67 (2018.01)
- G16H 10/20 (2018.01)
- G16H 10/60 (2018.01)
- G16H 50/20 (2018.01)
- A61B 5/103 (2006.01)
- A61B 5/024 (2006.01)
- A61B 3/113 (2006.01)
- A61B 5/16 (2006.01)
- A61B 5/08 (2006.01)

(52) U.S. Cl.
CPC .......... *A61B 5/1101* (2013.01); *A61B 5/1128* (2013.01); *A61B 5/742* (2013.01); *G06T 7/0016* (2013.01); *G06T 7/20* (2013.01); *G16H 10/20* (2018.01); *G16H 10/60* (2018.01); *G16H 20/00* (2018.01); *G16H 30/40* (2018.01); *G16H 40/67* (2018.01); *G16H 50/20* (2018.01); *G16H 50/30* (2018.01); *A61B 3/113* (2013.01); *A61B 5/024* (2013.01); *A61B 5/0816* (2013.01); *A61B 5/1032* (2013.01); *A61B 5/165* (2013.01); *A61B 5/4803* (2013.01); *G06T 2207/10016* (2013.01); *G06T 2207/20081* (2013.01); *G06T 2207/30004* (2013.01); *G06T 2207/30196* (2013.01); *G06T 2207/30204* (2013.01)

(58) Field of Classification Search
CPC .............. A61B 5/1125; A61B 5/14532; A61B 5/14542; A61B 5/162; A61B 5/4011; A61B 5/4017; A61B 5/4064; A61B 5/4803; A61B 5/6824; A61B 5/6826; A61B 5/6829; A61B 5/6892; A61B 5/0022; A61B 5/02055; A61B 5/021; A61B 5/024; A61B 5/026; A61B 5/0476; A61B 5/0816; A61B 5/091; A61B 2562/0219; A61B 5/4842; A61B 5/0077; A61B 5/0205; A61B 5/1101; A61B 5/1128; A61B 5/742; A61B 3/113; A61B 5/1032; A61B 5/165; G16H 50/20; G16H 20/70; G16H 40/60; G16H 40/67; G16H 10/60; G16H 50/30; G16H 20/00; G16H 30/40; G16H 10/20; G09B 19/00; G06T 7/0016; G06T 7/20; G06T 2207/10016; G06T 2207/20081; G06T 2207/30004; G06T 2207/30196; G06T 2207/30204
USPC ......................................................... 600/31
See application file for complete search history.

(56) References Cited

U.S. PATENT DOCUMENTS

| | | | |
|---|---|---|---|
| 8,781,856 B2 | 7/2014 | Hanina et al. | |
| 9,183,601 B2 | 11/2015 | Hanina et al. | |
| 9,454,645 B2 | 9/2016 | Hanina et al. | |
| 2006/0200007 A1 | 9/2006 | Brockway et al. | |
| 2007/0299910 A1 | 12/2007 | Fontenot et al. | |
| 2010/0169409 A1* | 7/2010 | Fallon | G06F 19/3418 709/203 |
| 2012/0316897 A1 | 12/2012 | Hanina et al. | |
| 2013/0028489 A1* | 1/2013 | Tracton | G06K 9/00536 382/128 |
| 2013/0345524 A1* | 12/2013 | Meyer | A61B 5/7271 600/301 |
| 2014/0276130 A1* | 9/2014 | Mirelman | A61B 5/744 600/483 |
| 2015/0130703 A1* | 5/2015 | Ghajar | G06F 3/013 345/156 |
| 2017/0164832 A1* | 6/2017 | Kaib | A61N 1/3968 |
| 2018/0052971 A1 | 2/2018 | Hanina et al. | |

OTHER PUBLICATIONS

EP Extended European Search Report in European Appln. No. 18857760.5, dated Nov. 12, 2020, 7 pages.

* cited by examiner

METHOD AND APPARATUS FOR DETERMINING HEALTH STATUS

CROSS-REFERENCE TO RELATED APPLICATION

This application claims priority to U.S. Provisional Application Ser. No. 62/560,523, filed on Sep. 19, 2017. The disclosure of the prior application is considered part of and is incorporated by reference in the disclosure of this application.

FIELD

This disclosure relates generally to monitoring patient health status and to the diagnosis and monitoring of disease employing visual and other interactions with live and automated systems, and more particularly to visually monitoring and predicting health status by observing a patient in response to a live or automated interview or other scripted or unscripted interaction to determine response to stimuli, and determine disease state. The disclosure additionally uses feedback from one or more additional measures of disease in order to tune the scripted or unscripted interactions, and allow for more precise and accurate determinations of disease state.

BACKGROUND

Diagnosis and monitoring of disease traditionally requires subjective determination of disease state by a healthcare professional. Application of known disease parameters to a currently observed set of disease states from a patient results in a diagnosis of disease. Continued monitoring of these disease states allows for monitoring of disease, and determinations of progression thereof, over time.

SUMMARY

Existing medical diagnosis and monitoring systems rely on subjective determinations, or upon measurements made in a controlled environment, such as blood draws in a clinic, x-rays and the like. As such, existing systems fail to describe the use of advanced visual analysis to properly diagnose and monitor disease, collecting information from across populations, and determining critical characteristics indicative of such diagnoses. These systems similarly fail to take into account accurate determinations of disease progression in order to optimize systems for future prediction of disease.

The subject matter of the present disclosure aims to address the drawbacks of the prior system by providing a system and method for analyzing a video sequence of a user performing one or more predetermined activity sequences to determine one or more features representative of one or more diagnostic attributes.

The contents of U.S. Pat. Nos. 8,781,856, 8,731,961, 8,666,781, 9,454,645, and 9,183,601 are incorporated by reference in their entirety in the disclosure of this application. The subject matter described in this specification is directed to a system, method and apparatus that allow for complete control and verification of adherence to a prescribed medication protocol or machine or apparatus use in a clinical trial setting, whether in a healthcare provider's care, or when self-administered in a homecare situation by a patient.

U.S. patent application Ser. No. 15/682,366 filed Aug. 21, 2017 to Hanina et al., titled METHOD AND APPARATUS FOR DETERMINING HEALTH STATUS, the entire contents of this application being incorporated herein, describes a system for determining health status based upon visual and other inputs, and a diagnostic system for incorporating visual and other sensor data for assisting in making such a diagnosis. The subject matter described in this application builds on these initial applications and provides one or more interactive systems for engaging patients to determine disease or progression of one or more characteristics of disease, and to utilize feedback from any such determined disease with other measurements of disease to improve and develop the interactive system to better perform these functions.

The subject matter described in this application builds on these previous applications and additionally provides a system in which a patient may be subject to the conduct of one or more interviews with an automated interviewer (e.g., a computing device such as a desktop, a laptop, a tablet, a mobile device, or any other device). These interviews are interactive and adaptive, allowing for the interviewer to collect data from the patient respondent, and adjust the content of the interview in response to the collected data. Through the use of such an adaptive design, indications of disease progression, changes in disease criteria or symptoms prompts additional interview questions or other interactions to further flush out details of these progressions or disease symptoms. The system may be scaled up or down, and can also allow for the segmentation of patient risk. That means the system can perform more or fewer steps as necessary. For example, if one particular symptom is noted to be changing, the system may scale up by taking additional measurements to further investigate the symptom. For example, if a patient has a higher temperature, the system may automatically perform additional tests to determine the source of the temperature increase.

The subject matter described herein further provides feedback to improve the interview and analysis system. Thus, other objective or proven measures of disease progression are correlated with interview responses, thus allowing for the improvement of the interview process, and also allowing for the focus of the disease progression and determination algorithms to more accurately predict disease progression. Indeed, correlation of responses to the interview process and other collected data with the outcomes of one or more known measures of disease allows for the validation of these analysis techniques, ultimately providing a more objective determination of disease and disease progression, and reducing reliance on, for example, subjective evaluation of response to validated assessment scales by trained raters.

Therefore, in accordance with one or more embodiments of the subject matter described in this specification, a system and method are provided in which a video sequence of a user performing one or more predetermined activity sequences, or performing routine activities, is analyzed to determine a number of features that may be representative of one or more diagnostic attributes, for example, eye movement, affect, heartrate, and skin tone. Such video sequences and other relevant collected data may be performed in response to a predetermined test sequence, or may be performed in response to an interactive interview presented to the patient, and performed by a live human interviewer, or an automated interview system. Once such features are recognized and tracked, a subsequent determination may be made to determine a subset or combination of these features that are indicative of diagnosis or monitoring of disease, and may be analyzed over time to determine changes in a particular disease progression. Such analysis may also be determined in accordance with a longitudinal analysis across one or more disease states.

Images or video sequences associated with a remote interview may be captured using an image capture device, for example, a dedicated camera or a camera embedded in a mobile device (e.g., a smartphone, a tablet, a laptop, or a smartwatch). In some embodiments, the image capture device is a single, stereo, or depth camera. In some embodiments, the image capture device includes additional sensors such as audio, motion, range or other sensors. Analysis processing may employ any methods, such as computer vision analysis, neural networks, deep learning, machine learning, or the like. Processing may be provided by a processor embedded within a camera, mobile device, or dedicated computing system, either local or remote, such as in a cloud-based system. Data transmission takes place over a cellular, Wi-Fi enabled or other wireless or wired communication system.

Various embodiments of the subject matter described in this application may include the use of 3D mesh tracking (for providing higher resolution tracking of any face or other body part movement, super high resolution action units (for monitoring detailed movement of the user), super high frame rate (to allow for higher resolution viewing and analysis of movement of the user, and video magnification (to allow for intense focus on the most important portions of one or more input images) as potential inputs. As will be further described below, the systems tracks and assesses patients over time based on a patient's current level of disease, or other variable. So system calibrates and identifies variances based on individual patient, and applies appropriate monitoring sequences based upon progression of the patient along one or more measurable variables.

The system also determines tone, type of questioning and is adaptive over time. The system does not just ask one validated scale but rather adjusts to patients responses, and may determine whether further, additional, or varied assessments should be applied to the patient. Such adjustments may include frequency, tone, intensity and intervention types, thus allowing for a varied experience by the patient. The system may further simulate nurse or other healthcare provider interactions. The system may therefore demonstrate empathy if patient is sick, and is adaptive to patient needs. The system is therefore interactive. The system is able to train patients to properly perform desired actions. Further, the system effectively monitors patients in either active or passive manners. In addition, the system intervenes with patients when determined to be appropriate, and is empathetic based on risk of the patient, and the current disease state of the patient. The system therefore establishes a bond with the patient, but also prompts the user, and is able to collect desired information from the user.

Based on a determined disease situation of the patient, and risk of disease progression, the system may capture some information more frequently and/or collect some other information less frequently. Such timing may be based upon recommendations for collection of information, based on a link to illness, or based upon an interactive multi-variable determination of best interval for administration. The system is further able to self-learn interactions based on monitoring of live nurses and care providers, as will be described in greater detail below. By observing actual human interaction, the system is able to monitor how to interact when performing particular tasks, or administering particular test sequences, and is able to simulate such interactions. Furthermore, if such interactions have a positive influence on disease or the health of the patient, such interactions may be employed in the future for any similar interactions. This information is provided to a learning engine to ensure empathy of the system, to support the system's ability to instruct patients to perform particular desired actions, and its ability to coordinate care.

Based upon the current state of a patient (i.e. demographic information current and historical disease progression, etc.), an inventive learning engine may also determine what types of assessments provide the most accurate results. Tone, speed, content of questions may be modified based on observation of human raters, assessors or care providers, and integration of these techniques when it is determined that such activities provide a positive response from patients. Thus, the system is able to listen to videoconference interviews, telephone interviews, or even in-person assessments to determine the most effective techniques, and to further determine techniques that provide the most positive response, based upon disease condition, or other categorizing information. Finally, collected data may be re-analyzed in response to newly-determined interaction techniques to further provide input to adjust actions of the system towards patients.

Still other objects and advantages of the subject matter described herein will in part be obvious and will in part be apparent from the specification and drawings.

The subject matter described herein accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the subject matter described herein will be indicated in the claims.

BRIEF DESCRIPTION OF THE DRAWINGS

For a more complete understanding of the subject matter described in this application, reference is made to the following description and accompanying drawings, in which.

DETAILED DESCRIPTION

In accordance with an embodiment of the present disclosure, a visual motion capture device, camera or the like is used to capture motion information related to the motion of a user, such as a medical patient, while performing one or more predetermined functions. These predetermined functions may be part of a script through which the user may be guided, may be a movement, speech, or other actions that may be reviewed while the user is performing one or more other tasks, or may be movement, speech or other action in response to an interview performed with the user. Such an interview may comprise a live interview with the user that is recorded and sensed by the recording and sensor devices, or may comprise an automated interview in which the user interfaces with a mobile or other device, the device simulating the actions of a human interviewer. The automated interview further includes one or more instances of branching logic, so that a measured response to a first question (including one or more of analysis of a visual, audio, or selection response) will result in a determination of a next question or set of questions to be asked. Automated interview questions may be asked over time, and across a number of patients, and therefore providing a baseline of the patient over time. Subsequent measurements are then able to determine changes in the patient activity over time. By further accumulating assessments over a number of patients over time, a general average baseline across all patients may similarly be provided. Finally, by segregating the accumulated patient information by demographics, disease state, or the like, baseline averages may be provided for each such segment, allowing for the determination of variances thereof indicative of changes in disease progression.

In U.S. patent application Ser. No. 13/189,518, filed Jul. 24, 2011 to Hanina et al., titled METHOD AND APPARATUS FOR MONITORING MEDICATION ADHERENCE, the entire contents thereof being incorporated herein, the present disclosure describes a system and method for providing a state machine that utilizes audio/video information to offer a population health tool to manage any number of patients, understand their behavior, and communicate and intervene when necessary or desirable. The system as set forth in the '518 application further employs machine learning to identify one or more trends and make automated judgments about patient states, as well as an ability to learn and highlight outliers or at risk populations. Thus, based upon captured information, patients may be placed into states that may aid in predicting those patients at risk for future hospitalizations, for example, or other types of situations where a varied intervention strategy may be beneficial. When considering large patient populations, such automated monitoring and categorization allows for monitoring of such patients, allowing managers to direct their attention to patients who might best benefit from such attention, and allowing the system to provide automated intervention when determined to be appropriate. This level of automated, intelligent intervention allows for effective management of patient behavior and medication adherence. Existing systems fail to capture patient behavior. Various embodiments of the inventive solution, including the described state machine, provide data relevant to medication adherence and other medical treatments as opposed to entire patient history, such as in an existing electronic medical record. Furthermore, the system acts as a video repository, recording administration by patients, and thus allowing for future review of such administration sequences by a manager or other healthcare professional if appropriate. Thus, upon determination by the system in a manner noted above, patients in one or more predetermined states may be indicated for such manual review by the manager or other healthcare provider. Finally, the system may be applicable not only to adherence information, but to any patient action or healthcare related treatment to which monitoring may be applicable.

The present disclosure additionally expands on these ideas, by using results of video, audio or other analysis techniques, to monitor user activities in response to a remote, automated interview process, for example, as place the user into a particular state in response to one or more of such analyzed responses, and additionally based upon one or more medically significant inputs (i.e., medical data such as a health status, disease state/condition, age, etc.) or a prior state of the user as related to the observation in question. Thus, upon placement of the user in a particular state, response to a particular interview question may result in the selection of a predetermined branching logic to move the automated interview in a particular direction, this resulting in a set of context and status based questions to be asked of the user.

In response to one or more actions captured and analyzed of the user in response to one or more of the posed automated interview questions, and additionally in accordance with the current state of the user, and additionally based upon one or more additionally collected pieces of information, a risk of patient behavior may be determined. Such risk may be associated with the user progressing along a particular disease, a risk of re-hospitalization, a risk of non-adherence to medication, or the like. Such risk may also be considered placing the user in a particular state that is defined by this higher risk profile. In response to this escalated risk profile, one or more desired responses may be implemented, such as a change in medication prescription, change in therapy, notification of a healthcare provider or caregiver, or a change in any other desired interaction with the user.

Information Capture and Analysis System

Figure 1:
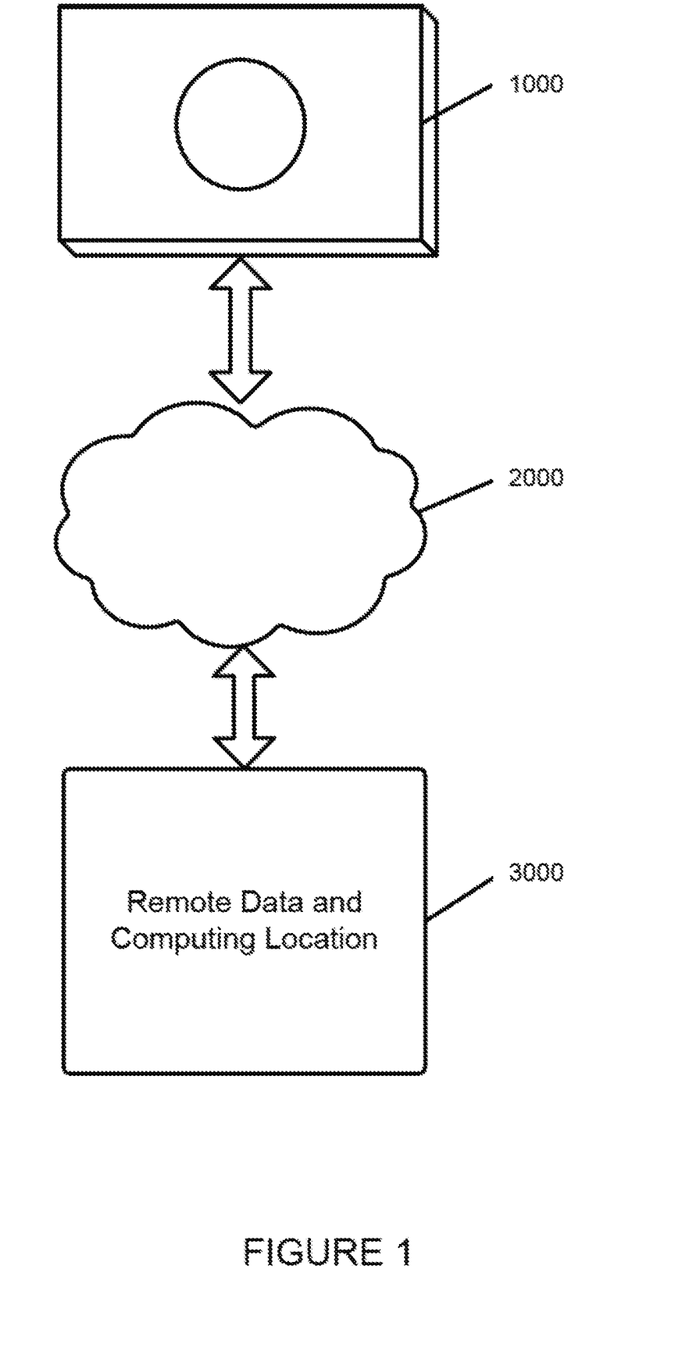
FIG. 1 is a block diagram depicting the details of an exemplary hardware configuration for implementing the system and method described in this application.

FIG. 1 illustrates an information capture and analysis system that includes a remote information capture apparatus 1000, a communication system 2000, and a remote data and computing device 3000. The information capture and analysis system is adapted to allow for the capture and processing of information in order to implement the system and method in accordance with the present disclosure. The information capture apparatus 1000 communicates with a remote data and computing device 3000 via a communication system 2000 (e.g., the Internet, Wi-Fi, LAN, WAN, Bluetooth, or other communication system). Via the communication system 2000, information captured by apparatus 1000 may be transmitted to remote data and computing device 3000, and analysis information or other instructions may be provided from remote data and computing device 3000 to apparatus 1000. It is further contemplated that a plurality of such information capture apparatuses 1000 may be coordinated to monitor a larger space than a space that can be covered by a single such apparatus. Thus, the apparatuses can be made aware of the presence of the other apparatuses, and may operate by transmitting all information to one of the apparatuses 1000, or these apparatuses may each independently communicate with remote data and computing location, which is adapted to piece together the various information received from the plurality of devices 1000.

Figure 2:
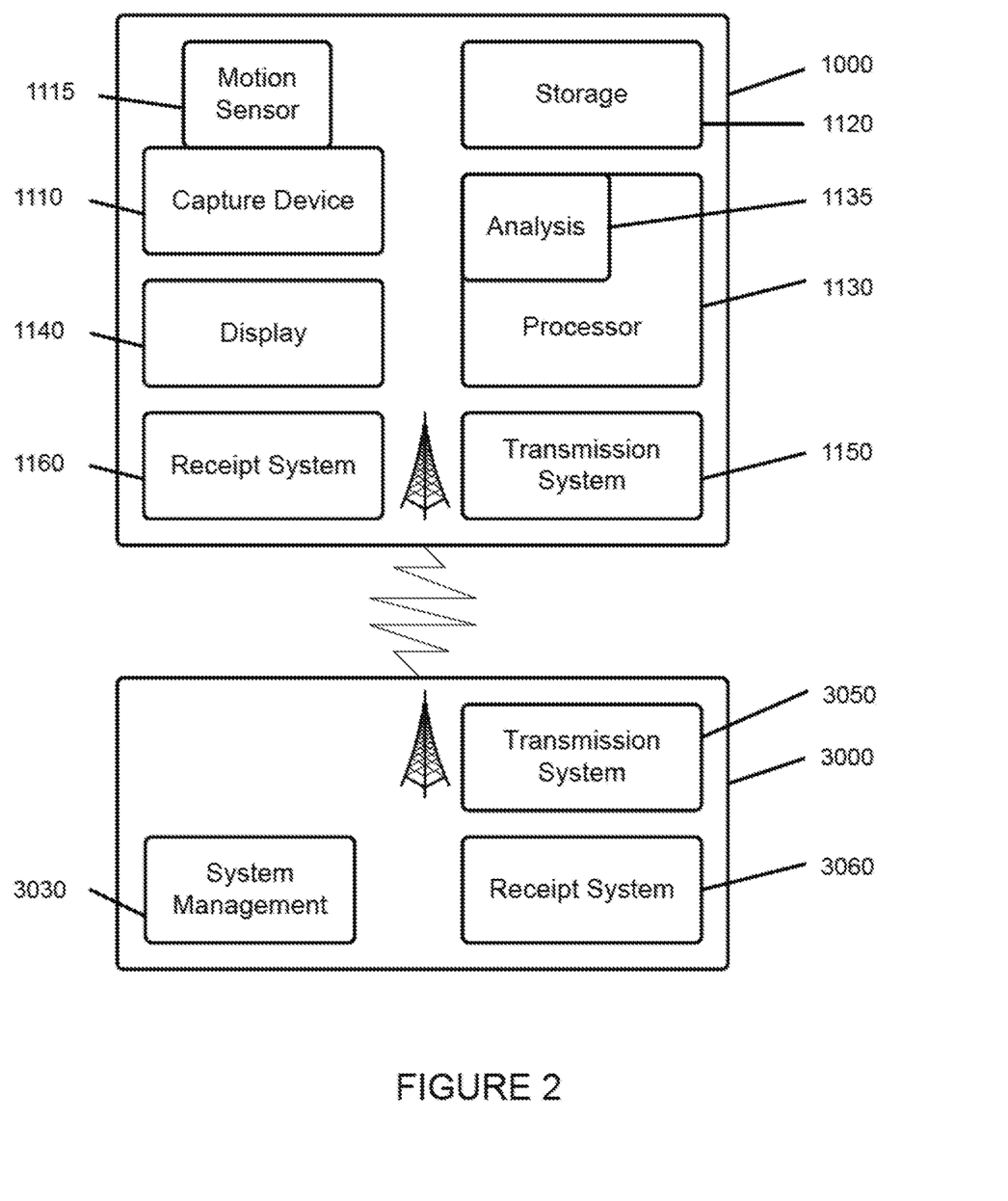
FIG. 2 is a block diagram depicting additional details of an exemplary hardware configuration for implementing the system and method described in this application.

FIG. 2 shows a more detailed view of an example embodiment of remote information capture apparatus 1000 and remote data and computing device 3000 of the information capture and analysis system of FIG. 1. As shown in FIG. 2, the apparatus 1000 comprises an information capture device 1110 for capturing video and audio data as desired. A motion detector 1115 or other appropriate trigger device may be provided associated with capture device 1110 to allow for the initiation and completion of data capture. Information capture device 1110 may comprise a visual data capture device, such as a visual camera, or may be provided with an infrared, night vision, or other appropriate information capture device. A storage location 1120 is further provided for storing captured information, and a processor 1130 is provided to control such capture and storage, as well as other functions associated with the operation of remote information capture apparatus 1000. An analysis module 1135 is provided in accordance with processor 1130 to perform a portion of analysis of any captured information at the remote information capture apparatus 1000. Apparatus 1000 is further provided with a display 1140, and a data transmission and receipt system 1150 and 1160 for displaying information, and for communicating with remote data and computing device 3000. In some embodiments, display 1140 may be used, along with an audio speaker, if desired, to provide one or more interview questions in accordance with an automated interview process. In such a situation, information capture device 1110 would then capture video and audio information provided by a user in response to the automated interview process.

The remote data and computing device 3000 comprises system management functions 3030, and a transmission and reception system 3050 and 3060 for communicating with apparatus 1000. Transmission and reception system 3050 and 3060 may further comprise various GPS modules so that a location of the device can be determined at any time, and may further allow for a message to be sent to one or more individual apparatuses, broadcast to all apparatuses in a particular trial, or being used for administration of a particular prescription regimen, of broadcast to all available apparatuses.

In accordance with an embodiment of the disclosure, apparatus 1000 is adapted to be part of a system that monitors user (patient) disease characteristics by way of passive monitoring, or actively requesting that the user be interviewed by the system, responses to the interview questions, as well as other movement comments or the like observed during conduct of the interview. Users of apparatus 1000 in accordance with this system give administrators a tangible and concrete manner in which to review activities and collected information. Apparatus 1000 of the disclosure is adapted to receive instructions, interview questions, or the like for patients from remote data and computing device 3000 and provide these instructions to patients or conduct an automated interview with the patients. Such instructions may comprise written, audio or audio/video instructions for guiding a user to perform one or more activities, such as performing a sequence of actions to test a particular action of the user, or whether a user is adhering to a prescribed medication protocol. The video instructions can be provided either by a real person or by an animated cartoon character (avatar), or the like.

The system, in accordance with an embodiment of the disclosure, is also applicable to monitoring of patient activities when being requested to perform particular actions in response to a remote, automated interview process, such as when performing such actions in order to simulate a predetermined measurement scale, such as may be used when assessing status of a particular disease. Such scaled may comprise one or more validated scales, typically administered by a healthcare provider, and correlated to provide insight to status of a disease. The conduct of a remote, automated interview will allow for the evaluation of a patient in relation to the particular disease without the need for a human to administer such a validated scale. Therefore, in accordance with an embodiment of the present disclosure, a method and system may be provided for analyzing captured patient motion data in near real time to provide feedback to the user (that is, the analysis is performed quickly enough to be able to provide feedback to the user while the system is still in use), to determine a number of times a participant performs some action that is, for example, considered suspicious, or to determine one or more elements of diagnosing or monitoring disease.

In accordance with a further embodiment of the present disclosure, the visual capture device 1110 may be used to capture visual information related to one or more users. Instructions about how a patient should be interviewed, proximity to camera, volume of response, etc. may also be provided. The operator or user may further be provided with the option to blur or make the screen opaque during interview process and collection of video, thus protecting the identity of a user captured therein.

Any standard camera or image capture device may be employed, including but not limited to a camera on a mobile phone, tablet, other computing device, standalone camera, or any other image acquisition apparatus that is able to record one or more (video) images of a subject. Audio and other characteristics may similarly be recorded along with the video, in accordance with the use of other appropriate sensor devices. In a preferred embodiment of the disclosure, the subject may comprise a face of a human, but may comprise any other desirable subject, including one or more other body parts of the user, or other object. Analysis of these recorded images may be performed currently, or the images may be stored for future analysis. Storage of such images may be performed local to the image capture apparatus, at a remote location, such as a dedicated storage location, or a cloud based storage system. Performance of automated interviews typically require near real time analysis of incoming data so that any branching logic may be applied, and the interview may continue. Of course, even after being analyzed locally, further remote analysis of the collected data may be performed.

Additionally, visual representations of a user can be further used to determine a status of the user in response to any request for activity in accordance with, for example, an automated interview. The system may perform a remote physiological exam based on touching the user's nose or holding up 3 fingers, for example. Visual determination of one or more parameters, such as motion, (body motion or camera motion with respect to still object), eye motion, skin tone, emotions, heart rate, breathing patterns (measured by video/depth image analysis or other devices), blood pressure, body mass, GPS location, proximity, or other measurements (such as non-visual measurements) that may be provided in accordance with one or more incorporated or coupled sensor, may be measured visually or otherwise, at once or over time, to determine changes in one more of such parameters in order to identify changes in the health of the user. In accordance with the conduct of an automated interview process, such parameters may be measured in response to one or more questions or request in the interview. Analysis of such responses may further allow for branching logic to be applied, and to guide the further direction of the interview. In accordance with an embodiment of the present disclosure, by way of example, display 1140 displays one or more bits of information to a user, such as a request in accordance with a predetermined interview. Such information may comprise a specific video sequence designed to test the reaction of the user, or may comprise interactive or other instructions to the user to perform a predetermined activity. Information capture apparatus captures information monitoring the user upon viewing of the displayed information, and performing one or more activities, or otherwise responding, in response thereto. Other devices for capturing information in response to presented visual, tactile, auditory, olfactory, gustatory or other stimuli may include diverse sensors, such a glucose meters, blood pressure cuffs, radar systems, visual capture devices, thermometers, accelerometers (measuring the shake of the hand of a user, for example), or the like. One or more of such measure parameters may be used to identify particular characteristics of one or more disease states. In such a manner, while monitoring adherence or other activities, or when performing actions in response to a presented test script or questions in an automated remote interview, such parameters may be measured, and reported back to one or more healthcare professionals, one or more care providers, other individuals, or may be collected in order to analyze automatically, perhaps over time, to diagnose and monitor disease. Thus, these parameters may be measured over time without reference to adherence, allowing for diagnosis of disease, measurement of progression of disease once diagnosed, or measurement of various health indicators to gauge the overall health of an individual.

Furthermore, a database or other repository of such measurements may be collected over time and over users at remote data and computing device 3000. Such database may be characterized by disease state or other demographic characteristics. In this manner future measurements of one or more users may be compared against such a database, and allow for diagnosis of one or more diseases, or changes in these characteristics when monitoring these diseases. Scales of responses to interview questions may also be stored in such a database, and allow for the determination of progression of disease, as well as correlation of responses to an automated interview with responses to questions during live administration of a validated scale testing for status or progression of disease.

The system may step up or step down levels of assessment based on risk profiles, so that users determined to be of a higher risk may receive more scrutiny. The system may also perform testing in accordance with passive monitoring in background based on visual information as the AiCure platform is used in normal functioning, as well as performing active assessments. In addition, if necessary, the system can go through a decision tree to offer tele-psychiatry when risk levels are high, or perform a simple check in when risk is low. If it is determined that a user has run out of medication (through calculation of adherence over time, or otherwise) automated delivery of medication may be provided, or if the patient needs to be remotely titrated, or changed to a different therapy. Optimization of the process will be achieved based on link to health outcomes (hospitalization events) captured from EMR or other data source, thus reinforcing actions and assessments that turn out to be the most accurate and helpful.

Furthermore, expected progression of such parameters or responses to questions over time may be determined for a population as a whole, or for various portions of a population, defined by demographics, disease state or the like. So, by way of example, it may be possible to determine expected progression of one or more visual characteristics, such as weight gain, of a female aged 40-60 suffering from diabetes, or to determine expected changes in response to a visual presentation of a script to be followed by a user. Progression of a visually measurable response may similarly be determined and correlated with progression of disease or other characteristic. Of course, other sub-populations may also be determined from such a database. Validated scales may further be employed to confirm progression of disease.

In yet a further embodiment of the disclosure, the determination of whether a particular user has modified disease characteristics may be determined in accordance with one or more unsupervised learning systems, such as a neural network or the like. In such a manner, the database of collected images may be employed to train such a system, identifying one or more characteristics from the training images that may be used to identify similar characteristics in future images. Additional information collected from one or more external sensors, such as accelerometers, voice recorders, or the like associated with the camera device, or one or more external medical devices, such as glucose meters, heartrate meters, or other measurement devices, or any other may be further included in the unsupervised learning system to additionally categorize images. This collected information may be used to calibrate the system during a learning phase, and may be subsequently removed during an operation phase. Combination of one or more of these readings with visual information may further allow for the determination of additional changes in status of a patient or user.

By way of example, pulse oximeters, heartrate monitors and the like may be employed with collected video information to allow for more precise determinations, in either an active or passive mode. Additionally, micro movements associated with movement of a mobile device or the like may also be employed. Micro eye movements, gaze tracking, analysis of expression, or any other micro gestures, micro movements, or other recognizable conditions and the like may further be employed. The AiCure system may monitor performance of such actions, and where the user is unable to perform such functions, may instruct the user on how to properly perform these actions. These additional measured features may be further employed to identify changes in characteristics along a number of alternative dimensions in such an unsupervised or supervised learning system, ultimately diagnosing or monitoring disease. Analysis of the accumulated information may allow for identification of one or more common characteristics among or between various disease states, demographic states, or other common identifying characteristic.

Longitudinal analysis of such data and changes in visual and other characteristics over time may be further correlated to negative health outcomes such as hospitalization events or death, and may give rise to relationships that can then act as the basis to trigger interventions in advance of a negative health outcome occurring. Through such monitoring, early warning signs may be extracted from visual images of users in a manner not previously possible. Thus, any number of visual analysis techniques may be employed to generate a video asset base by therapeutic area over time, thus allowing for the use of such assets to evaluate the health of users in the future including similar characteristics, and residing in similar therapeutic areas.

In accordance with one or more embodiments of the disclosure, it is anticipated that the use of one or more sections of the electromagnetic spectrum will allow for an in-depth analysis of facial or other visible user features. For example, as will be described below, rather than simply noting external facial features, use of the disclosure allows for the determination of the location of various blood vessels under the skin of a user in the field of view of a camera. Such analysis can be extended to any body part, and can be combined with any sequence of user-performed self-administration steps, or can be implemented with a care provider instructing actions to be taken. Over time, differences determined in the various images provide information about the performance of the user, and may further indicate changes in disease, physical ability, or the like. Such changes, for example, may be more visible under near-infrared light, or other wavelength of energy, thus resulting in additional information being extracted based upon the use of multiple types of light, energy, or other data extraction mechanisms.

The system may therefore learn various correlations between one or more observed features, and health status, health outcomes, disease progression, symptom progression, or one or more changes in overall health. By analyzing and correlating these changes in features and ultimate health status, the system provides a mechanism for determining yet unknown relationships between measurable quantities and the health of an individual. Once established, these relationships can then be used to predict future medical situations. By way of example, one or more sub-segments of the population may be targeted for observation. If such population is a post-stroke population, it is known that rapid weight gain may be a symptom of failure to take proper medication, or may predict a more urgent medical situation. In accordance with an embodiment of the disclosure, daily images of an individual may allow for a determination of such rapid weight gain without the use of a body-weight scale. In such a situation, a healthcare provider may be immediately notified to follow up with the individual. While visual-spectrum features may be used to determine weight gain, determinations of changes in pulse, blood pressure or other measurements may rely on the above-mentioned other areas of the electromagnetic spectrum, audio pulses, or any other type of desirable sensor, whether alone or in concert with a visual analysis.

In accordance with alternative embodiments of the disclosure, accumulated images of one or more users, associated sensor data information, visually extracted information, and one or more additional inputs may be incorporated into a comprehensive database. Analysis of the accumulated information may allow for identification of one or more common characteristics among or between various disease states, demographic states, or other common identifying characteristic. Human interactions may be further analyzed, and provided as further input into the system to determine the effectiveness of such interactions, and to allow the system to simulate human interactions with the user.

Such monitoring may take place in an active or passive monitoring situation, and may be provided on a mobile platform, and fixed computer system, or any continuous monitoring system.

Figure 3:
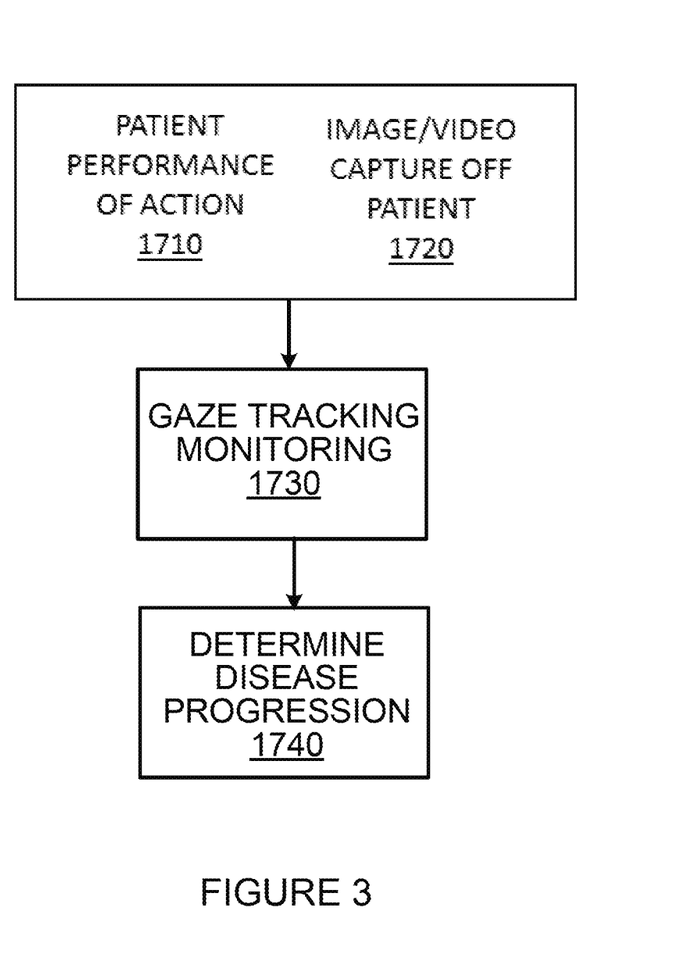
FIG. 3 is a flowchart diagram depicting additional details of an exemplary implementation of monitoring to determine disease progression.

FIG. 3 is a flow diagram of an example process for interviewing a user, monitoring the user during the interview to collect information about the user, and analyzing the collected information to determine one or more diagnostic attributes indicative of a disease or a change in a disease progression. The process is performed by a system of one or more computers located in one or more locations. For example, the information capture and analysis system of FIG. 1, appropriately programmed, can perform the process.

As shown in FIG. 3, in an active monitoring situation as part of an automated interview, the system automatically asks the user a sequence of questions in an interactive manner. Each of the question in the sequence following the first question is adaptive based on one or more of the responses of the user to the previous questions in the sequence. That is, the system automatically analyzes the content of the user's response to one or more previous questions in the sequence and then automatically generates the next question based on the content of responses. For example, users suffering from a particular disease might have a particular set of initial questions presented to them. Knowledge of the disease may be used to aid in the interpretation of responses to the questions. Responses to one or more of the questions in a particular manner may indicate a progression of disease in a direction that warrants follow up questions. A user suffering from Schizophrenia may be asked a set of questions to determine a general level of the disease. If answers to these questions, either actual response words or any observed actions while answering, indicate, for example, that negative symptoms are increasing (i.e. the user has a less animated response to the questions), additional questions may be presented in order to elicit additional information from the user to further flush out changes in symptoms of the disease. In another example, if someone is answering questions related to likelihood of suicide, answering questions a particular way may result in further follow up questions to determine a more precise risk of danger, and the need for help. It is the use of high level branching logic that allows the system to present an interaction that is able to extract the most critical details in an objective and scientific manner. Based on the answers of the user to these questions, the system asks the user to perform a particular set of actions, for example, actions for completing a medical test. The system may instruct the user to perform these actions on a mobile or other local device (e.g., the remote information capture apparatus 1000 of FIGS. 1 and 2) at step 1710. The system may display on a local device display (for example, the display 1140 of FIG. 3) one or more instructions to the user in accordance with a predetermined interview, and then captures (visual, audio, etc.) information related to the performance of the actions by the user at step 1720. Thus, if the user is to perform an eye movement test in response to one or more predetermined interview questions, on one embodiment, the system may instruct the user to watch an object such as a marker on a display. The system may display the marker on the display. The system can move the marker in a predetermined sequence around the display while the user is looking at the marker. This operation allows the system to measures the user's ability to maintain focus on a single item moving through a field of view. The system may monitor an eye movement ("gaze tracking") step 1730 to determine disease, or if the monitoring is performed over time by the system, the system can determine progression of disease as shown at step 1740. For example, the system determines disease or progression of disease based on the ability for a user to follow a moving object, or focus on a particular portion of a display screen or object. More specifically, the system may determine that slower tracking of a moving object by the gaze of the user is an indication of progression of a particular disease, such as symptoms of schizophrenia or other disease. Similarly, if gaze tracking is improved, the system may determine that a medication being administered is working to reverse disease progression. Of course, other questions, requests for actions, and observations may be employed as part of the automated interview process.

In an alternative embodiment, the system may ask the user focus on a particular marker on the display at step 1710. The system then provides on the display a second marker. The system measures the ability for the user to continue to focus on the initial marker at step 1730. The system thus can measure the user's ability to maintain focus, and how easily the user is distracted. Again, by monitoring the user over time, the system can determine progression of disease at step 1740.

In another alternative embodiment, the system may ask the user to hold a phone camera or other hand-held camera to focus on one or more static objects. When doing so, the system can use the relative motion of the still objects in the video (relative to the phone) to measure patient hand stability or tremor. In a manner similar to changes in gaze tracking noted above, the system can determine that the increases in tremor is an indication of a worsening condition in particular diseases, such as in Parkinson's or Alzheimer's disease. By measuring the relative tremor over time, the system can monitor symptom and disease progression. Similarly, if the system determines that tremors are reduced, the system can infer that the medication that the patient has taken is effective. By tracking an improvement of symptoms, the system may also obtain an evidence that a user is in fact properly administering the user's medication.

In a further embodiment of the disclosure, one or more correlations between responses provided by a patient in response to a remotely administered automated interview and an expertly administered validated assessment are determined. A validated assessment may be administered by a healthcare provider, and includes one or more questions or other activities that are predetermined to indicate level of disease, thereby providing the ability to compare the health status of a particular patient to that of a population as a whole. Such scales may include, for example, SMWQ/Study Medication Withdrawal Questionnaire for use to evaluate study medication withdrawal symptoms in therapeutic areas including mental disorders and chemically-induced disorders. A score provide after administration of this scale provides a score indicative of the level of medication withdrawal symptoms. Other scales allow for assessment of symptoms or disease progression for any number of diseases.

Such a comparison between the known responses to the validated scale, and the automated scale described in accordance with this disclosure may be made based upon analysis of a large number of interviews performed in comparison to known responses included in the validated scales, and may employ any of the structured or unstructured learning techniques noted above. As part of the noted correlation determination, to the system can evaluate scores of both expertly administered scores, and automatically administered interviews, using both visual and prosodic features, and passive sensor data (in the automated situation). In a controlled setting, such as a clinical trial, one may attempt to assign patients to one of two groups indicative of those taking a study drug, and one group in a placebo control group. Determination of an automated interview system that is able to consistently determine proper groups (as those in the placebo group should not see any benefit), would thus become an objective system for determining progression or regression of disease. The system may further comprise a learning engine for empathy, content, accuracy of assessment. The system therefore performs side by side to a human rater or care provider to capture interactions and learn how to simulate the interactions provided by the humans. In other words, a patient can first be evaluated by a doctor administering a validated scale, and then using the system provided in accordance with this disclosure. Results can be compared over time, and correlations between the validated scale and the automated system can be determined in order to confirm that accuracy and applicability of the automated system. The system is then able to proactively create a decision branch to make assessments that have the best outputs.

In addition to collecting information in an automated fashion related conduct of an automated interview, the system may employ one or more passive sensors in order to collect further information that may be correlated with interview responses, and further support determination of disease progression. Such passive data may include one or more of the following sensors or type of data collected: Speech duration, Geospatial activity, Kinesthetic activity, Sleep duration and quality data, Number, frequency and duration of phone calls, prosodic features, or other phone measured details, App usage (social, engagement, and entertainment), and one or more measurements of the ambient environment, and video recording of a daily activity like brushing teeth, combing hair, and/or taking medicine etc.

Figure 4:
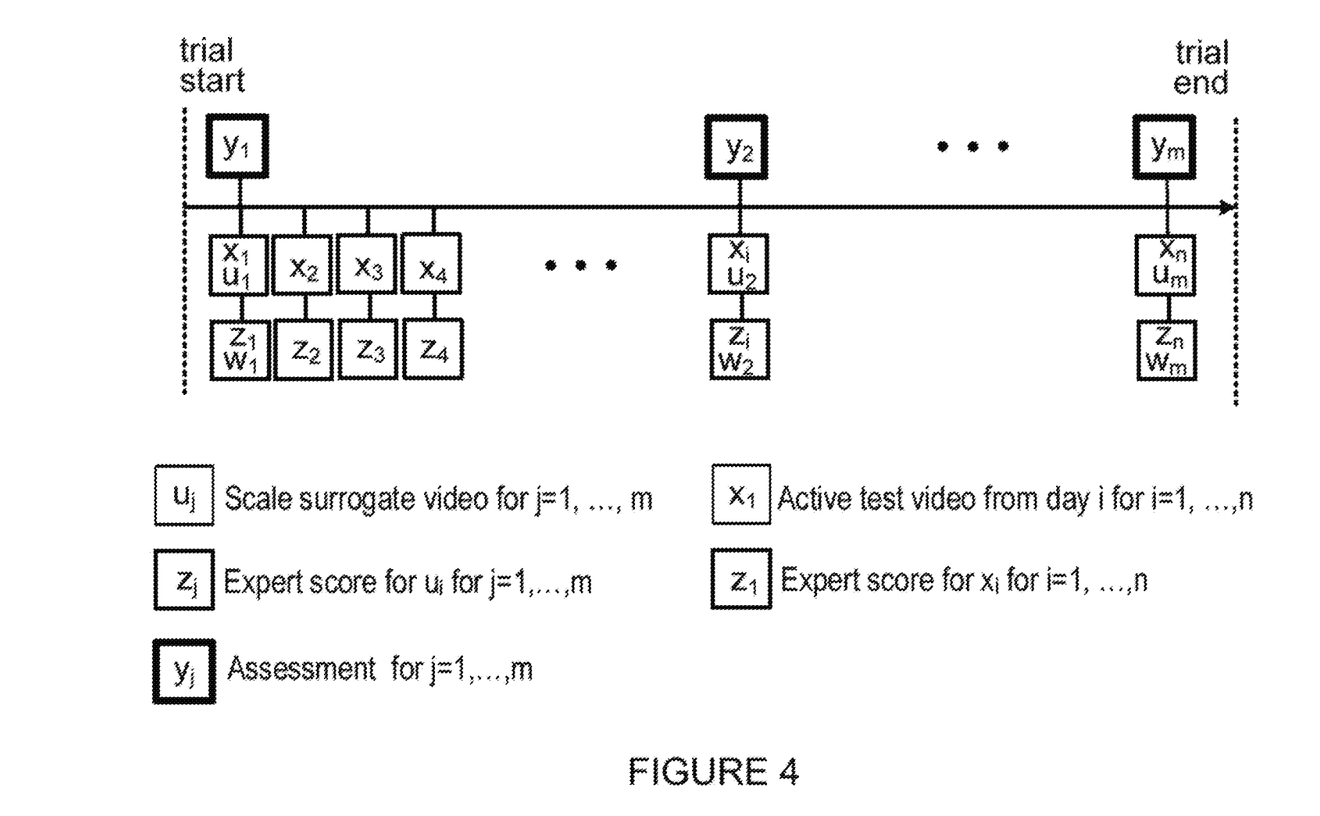
FIG. 4 is a timeline depicting a relationship between assessments.

Referring next to FIG. 4, a mechanism for evaluating one or more automated interview systems in accordance with an embodiment of the subject matter described in this specification is shown. For a predetermined period of time (trial start to trial end), one or more patients are evaluated upon visits to a healthcare provider (assessments Y), and is also interviewed by an automated interview system (measurements U), while a recorded version of responses to the automated interview may be scored by an expert (assessments W) at times corresponding to the healthcare provider visits. Thus, comparisons may be made to correlate the assessments Y from the healthcare provider and assessments W based on the recorded responses of the user to the automated interview (hereafter referred to as "automated responses"). Furthermore, a supervised learning system can be trained to automatically infer estimates of assessments Y, from measurements U and possibly taking advantage of assessments W either only during training or during training and testing. Additionally, between healthcare office visits, the automated interview measurements X, and expert scoring of recordings of these interviews (assessments Z) may similarly be correlated to determine further correspondence between the assessments. Measurements X can be taken more frequently and in a more "natural" setting they need not be restricted to a clinic setting. Measurements X need not necessarily consist of the same interview questions as in measurements U. When available, the supervised learning process can take advantage of measurements X and assessments Z in order to provide improved estimates of Y. In such a manner, the system allows for evaluation and comparison of any known, expertly administered test sequence (assessments Y in FIG. 4), and any automated interview and analysis system. Therefore, in accordance with this embodiment, human experts score recorded video interviews (based on standard scales, assessment Z). In parallel, the following may be extracted while the automated interview is being conducted, or in accordance with post-hoc analysis of recorded video. Extracted items may include, for example, one or more of:

Visual: action units, head pose, gestures, personal hygiene, etc.

Prosodic (speech tone): utterance duration, jitter, ratio of time speaking, pitch range, etc.

Natural language: histogram of keyword frequencies in transcribed text, "bag-of-words" etc.

It is thereafter possible to utilize one or more of supervised on unsupervised learning techniques to determine one or more correlations between disease progression, human scoring indicative of disease (for example, assessments Y in FIG. 4), and one or more extracted items. That is, the computer system can learn on various data inputs, including the answers to questions and final score of the expertly-administered scales, and the one or more extracted items or scores available from the automatically-administered system in order to determine progression of disease. In other words, the expertly-administered scales are designed to track disease progression. By correlating the automated responses to the expertly-administered scales, the system can learn to determine progression of disease based on the automated responses of the user.

Analysis of such presented interviews and scales may provide further possibilities to extract data. As noted above, collected data may be further analyzed to determine correlations between data collected and risk of patient progression of disease, or risk of one or more additional negative actions to be performed by the patient. Thus, observation of actions of a patient may be determined to be indicative of the likelihood of disease progression in the future, based upon observed progression from other patients in the past. For example, if an average patient shows that progression of a tremor for small to medium over a week, this may be indicative of a fast progression, while if this same progression takes two months, this may be indicative of a slow progression. Based upon this determination, a measured progression on a particular patient may then give insight into how quickly the patient may then progress on to a large tremor. Similarly, such a measured progression of tremor may also be indicative of a next symptom to be initiated. So, for example, tremors reaching a particular level may also indicate the initiation of changes in vision. The automated system described in this application aims to provide an automated system for analyzing patient responses, and to then measure disease progression, and predict likely future behavior.

Outcomes of correlation may be then used to determine risk profiles of patients, and may further be used to determine when a patient should be contacted or otherwise the subject of an intervention. This intervention may be performed by an alerted human, or may include a further automated system for intervening with a patient, and may present an appropriate additional interview based upon the current state and risk profile of the patient. These additional automated interview systems may include increased observation (or decreased) based upon one or more sensor types in accordance with estimates of disease. Thus, certain disease determinations may justify higher resolution monitoring (i.e. more frequently, or higher resolution video, depending on what is to be monitored. For example, motion, movement, emotion, etc. may be monitored more frequently (perhaps continuously) while capture of audio video responses to interview questions may be performed less frequently.

Figure 5:
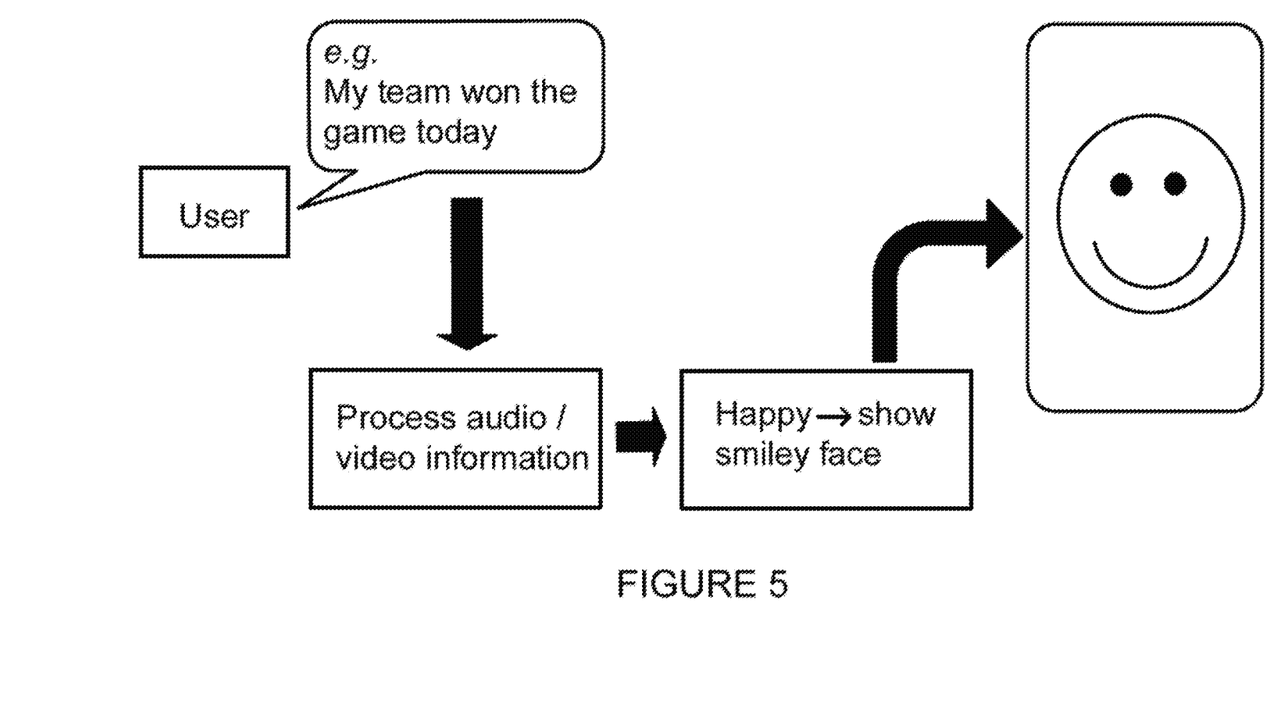
FIG. 5 is a flowchart diagram depicting an embodiment of the subject matter described in this application.

To make an automated interview appear as close to an in-person interview as possible, a selected neutral image with added animated expression can be used. A user's response or motion, as well as the interview questions, can be used to determine the animated expression. For example, as shown in FIG. 5, if a user says "I'm happy my team won the game!", a computer algorithm using visual, voice, and language analysis determines that the user is happy, then instructs a smiling expression to be added to the neutral image. When a user changes his/her position with respect to camera, the neutral face can also adjust its gaze to follow the user. The neutral image can be from, for instance, a preferred doctor, caregiver, family member, friends, celebrity, a cartoon character, or even abstract images. This approach can also be used for automated intervention systems.

Finally, once determinations of disease progression may be determined based upon the automated interviews, and accompanying analysis, actual patient outcomes (i.e. actual known progression of disease, comprises yet another data input (feedback system) that may be provided to the supervised or unsupervised learning system to allow for further training and modification of the system to better predict disease in the future.

Furthermore to the extent any such relationship between a measured characteristic and disease has not yet been defined, in accordance with an alternative embodiment of the disclosure, collected data may be processed to determine any such relationships to allow for use in the future. Different demographic groups may be employed to determine characteristics in these particular demographic groups, and thus allow for targeted diagnosis and monitoring of disease. The use of supervised or unsupervised learning techniques may be employed to analyze such data to determine any applicable relationships.

It should be noted that any of the above-noted embodiments of the disclosure may be provided in combination or individually. Furthermore, the system may be employed in mobile devices, computing devices, cloud based storage and processing. Camera images may be acquired by an associated camera, or an independent camera situated at a remote location. Processing may be similarly be provided locally on a mobile device, or a remotely at a cloud-based location, or other remote location. Additionally, such processing and storage locations may be situated at a similar location, or at remote locations.

Embodiments of the subject matter and the functional operations, for example, the remote information capture apparatus 1000 and remote data and computing device 3000 in FIGS. 1-2 and the processes described in detail above with reference to FIGS. 3-5, can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

While this specification contains many specific implementation details, these should not be construed as limitations on the scope of any subject matter described in this disclosure or on the scope of what may be claimed, but rather as descriptions of features that may be specific to particular embodiments of the subject matter described in this disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A system comprising one or more computers in one or more locations and one or more storage devices storing instructions that, when executed by the one or more computers, cause the one or more computers to perform operations comprising: providing, to a user interface displayed on a display of a user device, a sequence of questions for a user to respond to in an interactive manner, wherein each of the questions following a first question of the sequence of questions is adaptive based on the user's response to one or more previous questions in the sequence; capturing, by an audio sensor of the user device, one or more verbal answers to the sequence of questions; capturing, by a camera of the user device, motion and appearance of the user in a video sequence while the user provides the one or more verbal answers to the sequence of questions, the motion and appearance of the user being depicted in the video sequence; and analyzing the motion of the user in the video sequence and the one or more verbal answers to determine one or more indications of a disease or of a change in a disease progression.

2. The system of claim 1, wherein capturing the motion of the user comprises capturing one or more of the following: body motion, eye motion, emotions, heart rate, breathing patterns, skin tone, or speech tone of the user.

3. The system of claim 1, wherein the operations comprising:
based on responses of the user to the sequence of questions, selectively requesting the user to perform one or more actions to complete a medical test.

4. The system of claim 3, wherein capturing the motion and appearance of the user in the video sequence further comprises:
capturing further motion and appearance of the user while the user is performing the one or more actions to complete the medical test; and
wherein analyzing the motion of the user in the video sequence comprises analyzing the motion and appearance of the user while the user provides the one or more verbal answers to the sequence of questions and analyzing the further motion and appearance of the user while the user is performing the one or more actions to complete the medical test.

5. The system of claim 3, wherein requesting the user to perform one or more actions comprises asking the user to hold the user device such that the camera of the user device focuses on a static object.

6. The system of claim 5, comprising capturing camera motion of the user device with respect to the static object.

7. The system of claim 6, wherein analyzing the motion of the user in the video sequence to determine the one or more indications of the disease or of the change in the disease progression comprises:
measuring the user's hand stability or tremor based on the captured camera motion; and
determining the one or more indications of the disease or of the change in the disease progression based on the measured hand stability or tremor.

8. The system of claim 3, wherein requesting the user to perform one or more actions comprises asking the user to look at a moving object displayed on the user interface.

9. The system of claim 8, wherein capturing the motion and appearance of the user comprise capturing eye movement of the user while the user is looking at the moving object.

10. The system of claim 9, wherein analyzing the motion of the user comprises:
measuring the user's ability to focus on the moving object; and
determining the one or more indications of the disease or of the change in the disease progression based on the user's ability to focus on the moving object.

11. A computer-implemented method comprising:
providing, to a user interface displayed on a display of a user device, a sequence of questions for a user to respond to in an interactive manner, wherein each of the questions following a first question of the sequence of questions is adaptive based on the user's response to one or more previous questions in the sequence;
capturing, by an audio sensor of the user device, one or more verbal answers to the sequence of questions;
capturing, by a camera of the user device, motion and appearance of the user in a video sequence while the user provides the one or more verbal answers to the sequence of questions, the motion and appearance of the user being depicted in the video sequence; and
analyzing the motion of the user in the video sequence and the one or more verbal answers to determine one or more indications of a disease or of a change in a disease progression.

12. The method of claim 11, wherein capturing the motion of the user comprises capturing one or more of the following: body motion, eye motion, emotions, heart rate, breathing patterns, skin tone, or speech tone of the user.

13. The method of claim 11, further comprising:
based on responses of the user to the sequence of questions, selectively requesting the user to perform one or more actions to complete a medical test.

14. The method of claim 13, wherein capturing the motion and appearance of the user in the video sequence further comprises:
capturing further motion and appearance of the user while the user is performing the one or more actions to complete the medical test; and
wherein analyzing the motion of the user in the video sequence comprises analyzing the motion and appearance of the user while the user provides the one or more verbal answers to the sequence of questions and analyzing the further motion and appearance of the user while the user is performing the one or more actions to complete the medical test.

15. The method of claim 14, wherein selectively requesting the user to perform one or more actions comprises asking the user to hold the user device such that the camera of the user device focuses on a static object.

16. The method of claim 15, comprising capturing camera motion of the user device with respect to the static object.

17. The method of claim 16, wherein analyzing the motion of the user in the video sequence to determine the one or more indications of the disease or of the change in the disease progression comprises:
measuring the user's hand stability or tremor based on the captured camera motion; and
determining the one or more indications of the disease or of the change in the disease progression based on the measured hand stability or tremor.

18. The method of claim 13, wherein selectively requesting the user to perform one or more actions comprises asking the user to look at a moving object displayed on the user interface.

19. The method of claim 18, wherein capturing the motion and appearance of the user comprise capturing eye movement of the user while the user is looking at the moving object.

20. The method of claim 19, wherein analyzing the motion of the user comprises:
measuring the user's ability to focus on the moving object; and
determining the one or more indications of the disease or of the change in the disease progression based on the user's ability to focus on the moving object.

21. One or more non-transitory computer-readable storage media storing instructions that, when executed by one or more computers, cause the one or more computers to perform operations comprising:
providing, to a user interface displayed on a display of a user device, a sequence of questions for a user to respond to in an interactive manner, wherein each of the questions following a first question of the sequence of questions is adaptive based on the user's response to one or more previous questions in the sequence;
capturing, by an audio sensor of the user device, one or more verbal answers to the sequence of questions;
capturing, by a camera of the user device, motion and appearance of the user in a video sequence while the user provides the one or more verbal answers to the sequence of questions, the motion and appearance of the user being depicted in the video sequence; and
analyzing the motion of the user in the video sequence and the one or more verbal answers to determine one or more indications of a disease or of a change in a disease progression.

* * * * *